United States Patent [19]

Olsen et al.

[11] Patent Number: 5,705,162

[45] Date of Patent: Jan. 6, 1998

[54] FELV THERAPEUTIC AGENT, METHOD OF ITS PREPARATION, AND METHOD OF TREATING FELV INFECTION THEREWITH

[75] Inventors: Richard G. Olsen, London; John L. Ridihalgh, Columbus, both of Ohio

[73] Assignee: Parhelion Corporation, Columbus, Ohio

[21] Appl. No.: 543,820

[22] Filed: Oct. 16, 1995

[51] Int. Cl.$^6$ .................................................. A61K 39/21
[52] U.S. Cl. .................... 424/207.1; 424/819; 424/85.2; 435/386; 530/351
[58] Field of Search .................... 424/207.1, 85.2, 424/819; 530/351; 435/386

[56] References Cited

FOREIGN PATENT DOCUMENTS

WO23219  8/1995  WIPO.

OTHER PUBLICATIONS

Cotter, SM. 1992 Cancer Invest. vol. 10(2) 173–181.
Grant et al. 1984 Cancer Res. vol. 44: 498–502.
Zeidner et al 1993 J. Immunotherapy vol. 14:22–32.

*Primary Examiner*—Lila Feisee
*Assistant Examiner*—Julie E. Reeves
*Attorney, Agent, or Firm*—Mueller and Smith, LPA

[57] ABSTRACT

The present invention broadly relates to a therapeutic agent effective in mitigating disease associated with Feline Leukemia Virus (FeLV) in a feline infected with FeLV. A feline is an animal of the family Felidae. The novel therapeutic agent is composed of feline excised lymph nodes which have been subjected to mitogenic stimulation for their expansion dispersed in a pharmaceutically-acceptable carrier. Mitogenic stimulation conditions include culturing the excised lymph nodes in the presence of Interleukin-2. Optionally, culture conditions can include the presence of allogeneic or autologous FeLV tumor. The inventive therapeutic agent is prepared by excising lymph nodes from a feline infected the FeLV, mitogenically stimulating said excised lymph nodes for their expansion, and administering to the infected feline the expanded lymph nodes. Multidose regimens can be used as is necessary or desirable in convenient fashion. The method for mitigating disease associated with Feline Leukemia Virus (FeLV) in a feline infected with FeLV is composed of administering to the diseased feline the therapeutic agent composed of feline excised lymph nodes which have been subjected to mitogenic stimulation for their expansion dispersed in a pharmaceutically-acceptable carrier.

10 Claims, No Drawings

FELV THERAPEUTIC AGENT, METHOD OF ITS PREPARATION, AND METHOD OF TREATING FELV INFECTION THEREWITH

BACKGROUND OF THE INVENTION

The present invention relates to Feline Leukemia Virus that infects members of the Felidae family, and more particularly to a therapeutic or curative agent therefor. Vital-induced lymphoreticular neoplasms were first characterized in mice and rats, and later in chickens and turkeys. In 1964, viruses were also found to be associated with lymphoid malignancies of cats. The virus was named the Feline Leukemia Virus (FeLV). FeLV is classified as an oncornavirus (onco=oncogenic or cancer producing, and RNA= ribonucleic acid). This virus is very unstable in the environment and seldom survives for more than several hours at room temperature. It is inactivated by most disinfectants. FeLV occurs in three antigenically similar types, A, B, and C, or combinations of these types.

Infection results by contact between infected and susceptible cats. Infected cats may appear totally asymptomatic or they may manifest feline leukemia disease. The incidence of infected cats in the general population is somewhat variable, but has been reported to be as low as a few tenths of a percent to in excess of several percent depending upon locality. The incidence of infected cats in catteries is well known, FeLV-related diseases are much higher and have been reported to average 30% or more. The overall mortality to FeLV is proportional to the percentage of cats that become persistently viremic following exposure and infection. It is not surprising, therefore, that catteries and multiple-cat households have a greater loss than the general cat population because the carrier rate in these environments is much greater. In the general urban cat population, it has been estimated that the total death rate to FeLV could possibly be as high as 350 per 100,000. In catteries where FeLV is endemic, the death rate is potentially as high as 1 in 3 or more.

The pathogenesis of FeLV infection can be divided into three stages: primary disease, recovery or apparent recovery, and terminal illness. By and large, only those cats or kittens which become persistently viremic will show significant clinical signs of illness in the primary stage of infection. Clinical symptoms consist of varying degrees of fever, malaise, anorexia, weight loss, generalized lymphadenopathy, and hematological abnormalities. Death can occur in the primary stage of infection and when it is usually a direct consequence of severe bone marrow suppression and/or secondary infection. Cats that recover completely from the infection usually do not show any clinical or hematological abnormalities in the primary stage of the disease. In contrast, kittens or cats that develop clinical and hematological abnormalities during the primary stage of the disease usually become persistent virus carriers. It is interesting to note that relatively few kittens or cats die as a result of this primary illness. In fact, most persistently infected cats will apparently recover from these primary symptoms, giving the veterinarian and the owner a false sense that recovery is complete and that the virus has been eliminated. Carrier cats may remain asymptomatic for weeks, months, years, or even an entire natural lifetime. Many of these cats, however, will eventually develop some FeLV-related disease.

Persistent virus carrier cats can be expected to develop a fatal FeLV-related illness at the rate of about 20% per year for every year they remain infected. The mortality can be greater if symptomatic treatment is not given, or if the animals are stressed. This means that about 50% of chronic FeLV carriers will be dead within four years or less. In addition to a fatal disease, persistent virus carriers frequently suffer from vague persistent or intermittent illness and secondary infections of a number of types. Those diseases related directly to the effect of the virus include neoplastic disease, bone marrow suppressive disorders, immunological disorders, reproductive problems, and various miscellaneous diseases. Those diseases indirectly related to FeLV infection include viral and bacterial secondary infections, protozoal diseases, and other maladies. In terms of total disease caused by FeLV, vague illness and secondary infections are the most frequent. This is followed in order of frequency by bone marrow suppressive disorders, lymphoproliferative neoplasms, and myeloproliferative disease. Further information on FeLV can be found in Olsen, et al., *Comparative Pathobiology of Viral Diseases*, Vol. II, CRC Press, Inc., 1985, the disclosure of which is expressly incorporated herein by reference.

The singular vaccine effective for preventing FeLV is that of Olsen as disclosed in U.S. Pat. Nos. 4,332,793 and 4,434,157, the disclosures of which are expressly incorporated herein by reference. Despite the success of such vaccine, ameliorating, if not curing, disease caused by FeLV is a goal that has eluded the art.

BROAD STATEMENT OF THE INVENTION

The present invention broadly relates to a therapeutic agent effective in mitigating disease associated with Feline Leukemia Virus (FeLV) in a feline infected with FeLV. A feline is an animal of the family Felidae. The novel therapeutic agent is composed of feline excised lymph nodes which have been subjected to mitogenic stimulation for their expansion dispersed in a pharmaceutically-acceptable carrier. Mitogenic stimulation conditions include culturing the excised lymph nodes in the presence of, for example, Interleukin-2. Optionally, culture conditions can include the presence of, for example, allogeneic FeLV tumor. The inventive therapeutic agent is prepared by excising lymph nodes from an FeLV infected feline, mitogenically stimulating said excised lymph nodes for their expansion, and administering to the infected feline the expanded lymph nodes. Multidose regimens can be used as is necessary or desirable in convenient fashion. The method for mitigating disease associated with Feline Leukemia Virus (FeLV) in a feline infected with FeLV is composed of administering to the diseased feline, an effective amount of the therapeutic agent composed of feline excised lymph nodes which have been subjected to mitogenic stimulation for their expansion dispersed in a pharmaceutically-acceptable carrier. Multiple cellular administration of the therapeutic agent with a suitable time period therebetween may find advantages in accordance with the present invention additionally.

Advantages of the present invention include the development of a therapeutic agent effective in reversing the ravages of FeLV in felines infected with FeLV. Another advantage is the relative simplicity by which the therapeutic agent can be prepared. A further advantage is the successful implementation of an adoptive cellular therapy approach to the mediation/cure of FeLV. These and other advantages will be readily apparent to those skilled in the art based on the disclosure set forth herein.

DETAILED DESCRIPTION OF THE INVENTION

Heretofore, adoptive immunotherapy has provided an attractive treatment modality for human cancer therapy.

Using lymphokines such as Interleukin-2 (IL-2) and lymphokine-activated killer cells (LAK) derived from patient peripheral blood, Rosenberg, et al. demonstrated that a small but significant percentage of patients with melanoma and renal cell cancer achieve a long-lasting response. Rosenberg, et al., "Adoptive Cellular Therapy: Clinical Applications", *Biologic Therapy of Cancer*, DeVita, et al. (Eds.), J. B. Lippincott Company, Philadelphia, Pa., 1991. A second approach to adoptive immunotherapy has been to expand lymphocytes from tumors in culture. Rosenberg, "Adoptive Cellular Therapy: Clinical Applications", *Biologic Therapy of Cancer*, DeVita, et al. (Eds), J. B. Lippincott Company, Philadelphia, Pa., p. 241 (1991); Topalian, et al. "Tumor Infiltrating Lymphocytes: Evidence of Specific Immune Reactions Against Growing Cancers in Mice and Human", *Important Advances in Oncology* 1990, DeVita, et al. (Eds), J. B. Lippincott Company, Philadelphia, Pa., p. 19 (1990), and Rosenberg, et at., "Use of Tumor-Infiltrating Lymphocytes and Interleukin-2 in the Immunotherapy of Patients with Metastatic Melanoma", *N. Engl. J. Med.*, 25:1671, 1988. Using these tumor-infiltrating lymphocytes (TIL), several research groups have documented superior tumor cytolytic activity and better trafficking of these TIL cells to tumor than LAK cells. Rosenberg, et al., *N. Engl. J. Med.*, id.; Dillman, et at., "Continuous Interleukin-2 and Tumor-Infiltrating Lymphocytes as Treatment of Advanced Melanoma", Cancer, 68:1, 199 1; Kradin, et al., "Tumor-Infiltrating Lymphocytes in Interleukin-2 in Treatment of Advanced Cancer", Lancet, 33:577, 1989; and Bukowski, et al., "Clinical Results and Characterization of Tumor-Infiltrating Lymphocytes with or without Recombinant Interleukin-2 in Human Metastatic Renal Cell Carcinoma", *Cancer* Res. 51:4199, 1991. Overall, these TIL cells appear to be therapeutically effective for patients with melanoma. Tumor-infiltrating lymphocytes have been generated from many solid tumors, including colon and breast cancer, however, these cells do not appear to mediate tumor-specific cytolytic activity in vitro and it remains to be determined if these cells will be effective in adoptive immunotherapy models. Rosenberg, "Gene Therapy of Cancer", Important Advances in Oncology, 1992, DeVita, et al. (Eds), J. B. Lippincott Co., New York, N.Y., pp 17–18, 1992.

Several problems—including the difficulty of obtaining TIL cells from most solid tumors such as breast and colorectal cancer, the type of lymphocytes which expand under these conditions, and the long periods of culture time needed to generate TIL cells—have made widespread application to most tumors prohibitive. An alternative source of tumor lymphocytes may be lymph nodes. Several laboratories have demonstrated a tumor-specific immune response in regional lymph nodes from cancer patients, including breast, head and neck, pancreas, and colon. Hoover, et al., "Activation and In Vitro Expansion of Tumor-Reactive T Lymphocytes from Lymph Nodes Draining Human Primary Breast Cancers", *J. Surg. Oncol.*, 46:117, 1991; Cozzolino, et al., "Characterization of Cells from Invaded Lymph Nodes in Patients with Solid Tumors, Lymphokine Requirement for Tumor-Specific Lymphoproliferative Response", *J. Exp. Med.*, 166:303, 1987; Barnd, et al., "Specific, Major Histocompatibility Complex-Unrestricted Recognition of Tumor-Associated Mucins by Human Cytotoxic T-cells", *Proc. Nat. Acad. Sci. USA,* 86:7159–7163, 1989; and Vose, et al., "Tumor Reacting Lymphocytes Stimulated in Mixed Lymphocyte and Tumor Culture", *Cancer Immunol. and Immunother.*, 15:227–236 (1983). In experimental mice models, regional lymph nodes have been shown to contain tumor-specific pre-effector cells which, when expanded in vitro, can eliminate experimental metastases. Yoshizawa, et al., "Activation by Anti-$CD_3$ of Tumor-Draining Lymph Node Cells for Specific Adoptive Immunotherapy", *Cell Immunol.*, 134:473, 1991; and Yoshizawa, et al., "Specific Adoptive Immunotherapy Mediated by Tumor-Draining Lymph Node Cells Sequentially Activated by Anti-$CD_3$ and IL-2", *J. Immunol.*, 147:729, 1991. In animal (mice) models, the timing of lymph node removal and the size of primary (implanted) tumor are critical factors in the ability to detect pre-effector lymphocytes. Yoshizawa, et at., "Activation by Anti-$CD_3$ of Tumor-Draining Lymph Node Cells for Specific Adoptive Immunotherapy, supra; and Sakai, et al., "Phenotype Analysis in Cellular Mechanisms of Pre-Effector T-Lymphocyte Response to a Progressive Syngeneic Murine Sarcoma", *Cancer Res.*, 50:4371–4376, 1990. These lymphocytes also can be expanded in vitro in the absence of tumor stimulation by using sequentially anti-$CD_3$ and IL-2.

The present invention is not directed to experimental (implanted) metastases in mice, nor to solid tumors per se. Rather, the present invention is directed to feline leukemia. Thus, while the art continues to study adoptive cellular therapy techniques for the treatment of human cancer and uses animal models in such studies, the present invention documents the successful application of adoptive cellular therapy to feline leukemia for its mediation; if not in some cases, its outright cure.

Conventional diagnosis of feline leukemia often is rendered by the attending veterinarian using commercial ELISA kits, immunofluorescent antibody assays of peripheral blood smears, or plasma FeLV antibody status by an ELISA assay often is appropriate in order ensure that the diseased feline is infected with FeLV. As in initial step of the process, then, the diseased feline is administered anesthesia and lymph node(s) removed in accordance with conventional veterinary medicine practice. To date, it does not appear important which class of lymph nodes are removed. Popliteal lymph nodes have been used for convenience.

The excised lymph node lymphocyte (LNL) cells then are expanded or proliferated in cell expansion regimens as taught herein. Briefly, cell expansion involves the steps of dissociation of LNL from lymph node tissue; ex vivo activation and initiation of cell expansion; media changes, cell culture splitting; and cell harvest and preparation of final product for administration to the diseased feline.

Cell and tissue dissociation is accomplished conventionally, such as by centrifugation, in order to harvest the LNLs. Initiation of cell expansion includes the initial use of a serum media as is convention in cell expansion regimens. Additionally, mitogenic stimulation most preferably is conducted using IL-2, as soluble anti-$CD_3$ used in ACT (adoptive cellular therapy) heretofore were determined to not be mitogenic for lymph node cell expansion. Aliquots of fresh media and cytokine are periodically added to the culture during their growth. Optionally, inactivated allogeneic FeLV infected cells can be included in the growth media, as the examples will demonstrate.

Desirably, at least about $10^7$ cells are produced for administration to the diseased feline. Autologous expanded cells presently are preferred for use in administering to the diseased feline from which the lymph nodes were removed. Administration of the therapeutic agent thereafter is accomplished. Side effects from the administration of the novel therapeutic agent appear to be minimal—slight elevation in temperature—which makes the invention that more valuable. Most human adoptive cellular therapy regimens have been reported to be quite noxious, if not toxic, to the patient as is the administration of large doses of cytokines, e.g., IL-2.

In the data presented below, lymph node (ln) cells were treated initially with both IL-2 and anti-CD-3 for 24 hours, exposed to low numbers (1:100 virus infected cells to ln cells) of heat-inactivated virus infected cells. The cells then were cultured in IL-2 only. Because the FeLV infected cats used in the study were systemically infected, allogeneic FeLV infected cells were used to activate (sensitize) the ln lymphocytes. Note, that this method differs from ACT studies in tumor bearing subjects, animal or human, in that the pre-effector ln cells are sensitized to allogeneic virus infected, cells and not isogeneic, tumor cells and expanded for infusion.

Eighteen cats used in the study were infected with FeLV at inception of therapy. Five of the cats died—one died 2 days after removed of ln and prior to treatment (Sheba, Cat no. 5), one died 3 days post-infusion (C.E., Cat no. 8), days post-infusion one died 53 days post-infusion (Chubber Baby, Cat no. 2), one died 2 months post-infusion (Susie, Cat no. 9) and one died 36 days post-infusion with bone marrow aspirate suggesting that death may been unrelated to leukemia (Half-Pint, Cat no. 3). Thus, there were 13 evaluable cats in this study.

More important than the cats that died are the cats that have survived to date. Two of the cats (Star and Taffy) were moribund and between Stage III and IV when treatment was initiated. One cat (Lady Jane) was FeLV positive at initiation of therapy. Star was moribund at initiation, virus positive, and losing weight. Two weeks post infusion, she was clinically normal and has remained normal for approximately 8 months. More remarkable is the cat's virus status. Both salivary assays and peripheral blood lymphocyte (PBL) smears showed loss of viral antigen. The PBL has remained negative while the ELISA assay with saliva was weakly positive. On Jan. 20, 1995, the cat weighted 7.5 lbs and remains in good health. Taffy, the second moribund cat, was treated and while its virus status has remained positive, its overall health has been excellent. The cat has gained weight form 7.75 to 8.75 lbs when last examined and all clinical parameters were normal 97 days post-treatment.

EXAMPLES

IN THE EXAMPLES

Materials and Methods

The following method was used to expand the excised feline lymph nodes.

1. Lymph nodes were aseptically removed from the cat and placed immediately in RPMI 1640 medium containing 100 µl g/ml gentamicin and 20 µg/ml Fungizone and supplemented with 20% fetal bovine serum (FBS) (Transport Medium), and placed on ice for transport.

2. In a laminar flow hood, the lymph nodes were placed in 60 cm petri dishes, and fat and extraneous tissue were removed with a scalpel.

3. The lymph nodes were expressed with a sterile 5 ml plunger until they burst.

4. The cells were pipetted and washed from the dish with RPMI 1640 medium, and centrifuged at 200×g for 5 minutes.

5. The supernatant was discarded and the cell pellets were resuspended in 10 ml of RPMI 1640 containing: 20% fetal bovine serum (heated at 56° C. for 30 minutes), 50 µg gentamicin/ml, 2 mM glutamine, and 1% sodium pyruvate (this growth medium, GM, was used for all experiments reported herein).

6. The suspended cells were counted by diluting 0.1 ml of cell suspension in 0.9 ml PBS, then diluted with 1 ml of 0.2% trypan blue. Cells were counted in hemocytometer and adjusted to $1.0 \times 10^6$ cells per ml in GM containing 500 IU human recombinant IL-2 (hR-IL-2) or 100 units/ml of commercially prepared non-recombinant IL-2, and 50 ng of anti-CD-3 monoclonal antibody (MoAb) and incubated 24 hours at 37° C. in T flasks.

7. At the end of this incubation period, cells were centrifuged at 200×g for 5 minutes. The supernatant was discarded and cells were resuspended at $5 \times 10^5$ ln cells/ml in GM supplemented with 500 IU IL-2. FL 74 cells were heated at 56° C. for 10 minutes to kill the cells, then added to the ln cultures at a ratio of 1 FL74 cell/100 ln cells. The cell mixtures were incubated at 37° C. for 72 hours.

8. At the end of this incubation period, cells were re-adjusted to $5 \times 10^5$ cells/ml and incubated for 72 hours.

9. At 48 hours incubation time, 0.1 ml of cells and medium were added to brain heart infusion broth and to Saboraud-Dextrose broth to assure cultures were bacteria and fungi-free.

10. At the end of 72 hours incubation time, the cells were centrifuged and resuspended in 20 ml of sterile PBS containing 1.25% bovine serum albumin (BSA). Total cell counts were determined and the inoculum was transported on ice to the clinic for infusion. It should be noted that 3 cat cell cultures also were prepared without FL74 cells.

FeLV assays were conducted following manufacturers instructions for the FeLV ELISA assays and peripheral blood smears were stained by indirect immunofluorescent antibody assay. The primary antibody was goat anti-etherdisrupted purified FeLV antibody and the secondary reagent was rabbit anti-goat IgG serum diluted to working concentrations.

For PCR analysis, $10^6$ lymph node cells were centrifuged after overnight incubation and at harvest—usually 1 and 7 days—and the pellet resuspended in 1.0 ml cold GM containing 10% DMSO. The cells were ampouled and frozen overnight at $-20°$ C. and transferred the next day to $-80°$ C. until all the samples were collected. The samples were sent frozen on dry ice by overnight carrier to Engene Biotechnologies (San Diego, Calif.) for PCR analysis for FeLV gene sequences.

Experiment Cats

Cats were selected for therapy based on FeLV persistent infection as determined by at least 2 positive serum or saliva ELISA tests (using commercial ELISA kits), and at least one positive immunofluorescent antibody assay (IFA) on peripheral blood smears. Client cats were volunteered for study after consultation with their veterinarian and evaluation for virus infection and clinical symptoms. Cats were selected for treatment based on FeLV persistent infection as determined by commercial ELISA kits, immunofluorescent antibody assay (IFA) of peripheral blood smears, and antibody/plasma FeLV antibody status by an ELISA assay. The clinical condition of the cats was determined after examination and clinical tests under the supervision of state licensed veterinarians.

Cats were staged as to severity of the disease by the following clinical parameters in addition to virus status:

1. Weight
2. Temperature, pulse, and respiration (TPR)
3. Blood Urea Nitrogen (BUN)

4. Glucose
5. Urinalysis
6. Packed Blood cell Volume (PCV)
7. Total serum proteins Based on the above-tabulated parameters, the experimental cats were staged from I through IV, as follows:

| STAGES OF FeLV DISEASE | |
|---|---|
| Stage I | Asymptomatic, afebrile |
| Stage II | Mild signs of disease (depression, intermittent low-grade fever, normal PCV, not eating |
| Stage III | Moderate signs of disease (depression, lethargy, persistent fever, febrile, mild anemia, not eating |
| Stage IV | Severe signs of disease (depression, anorexia, marked weight loss, dehydration), afebrile or febrile, anemia, not eating |

Cats Inoculations

1. Pre-inoculation: Clinical parameters and FeLV status were determined prior to infusion of cells.
2. Cats were prepared for surgery and anesthetized with Ketamine (100 mg/ml concentration)—usually 1.0 ml.
3. The area over the cephalic vein was shaved, antiseptically cleansed and an IV catheter (22 or 24 ga) inserted in the vein. The cell inoculate was pre-warmed and shaken to re-suspend the cells and slowly infused (about 1.5 to 10 minutes). The catheter was removed and blood flow stopped by pressure application and the cat was returned to the cage. The cats usually "spiked" a temperature about 1 hour post-inoculation. Cats were observed hourly until their temperature returned to a normal range.

The total number of cats enrolled in the study was 20 with 13 being evaluable. Of note, two of the cats were normal FeLV negative and not used in the study while one of the cat's cells were contaminated in culture and, thus, not used. Of the 7 cats (out of 20 enrolled in the study) that died, 1 died 2 days after ln removal (Cat 5) and before therapy could be initiated; 1 died during perfusion (Cat 16), 1 died 3 days post-infusion (Cat 8), and 4 cats died 1.5 months (Cat 3), 2 months (Cat 9), 2.5 months (Cat 17), and 3.0 months (Cat 2) after therapy. It should be noted that Cats 2 and 3 had an improvement in their quality of life prior to death. Thus, the following cats were not evaluable and are not reported herein: 5, 6, 8, 9, 11, 15, and 16.

Of importance, however, are 10 cats currently are clinically healthy and appear normal with 5 of these cats having reverted from FeLV positive to FeLV negative status. The results recorded are set forth below.

EXAMPLE 1

CAT 1

"Lady Jane", a 6 month old clinical normal (Stage I) intact domestic short hair (DSH) female cat, tested positive for FeLV on Apr. 20, 1994. On Jun. 23, 1994, one popliteal lymph node was aseptically removed under general anesthesia and propagated in GM containing IL-2 (100 U/ml) and anti-CD-3 MoAb (50 ng/ml). The cells were incubated at 37° C. and on the second day, the culture was divided in half. One culture was incubated with an established FeLV persistent-infected lymphoid cell line, FL-74, at a 1:1 ratio. The second culture was incubated in the absence of FL-74 cells. Fresh GM was added as shown in Table 1 below. Ten days after initiation of the cultures (Jul. 3, 1994), cells were counted, centrifuged, pooled, and resuspended in 1.0 ml of PBS plus 1.25% bovine serum albumin, and infused (3.51× $10^7$ cells) intravenously into Lady Jane. The growth and viability of the lymph node cells are shown in Table 1 below. The results of the post-inoculation virus assays are shown in Table 6 below.

TABLE 1

| | Incubated with FL-74 Cells | | | Incubated without FL-74 Cells | | |
|---|---|---|---|---|---|---|
| Day in Culture* | Living (× $10^7$) | Total (× $10^7$) | % Viable | Living (× $10^7$) | Total (× $10^7$) | % Viable |
| 1 | 0.78 | 15.0 | 100 | 0.78 | 15.0 | 100 |
| 2 | 9.12 | 15.4 | 60 | N.D.* | N.D. | N.D. |
| 3 | 2.4 | 8.04 | 30 | 3.69 | 4.22 | 87 |
| 4 | 2.7 | 8.51 | 31 | 3.42 | 4.18 | 82 |
| 5 | 2.6 | 8.77 | 29 | 2.28 | 2.90 | 79 |
| 6 | 0.89 | 2.73 | 25 | 1.67 | 2.30 | 73 |
| 7 | 0.63 | 3.14 | 20 | 0.64 | 1.62 | 40 |
| 8 | 0.39 | 2.08 | 19 | 0.39 | 3.79 | 10 |
| 9 | 0.27 | 1.78 | 15 | 0.143 | 1.35 | 10 |
| 10 | 0.082 | 2.3 | 4 | 0.061 | 1.25 | 5 |

*Day 3 - FL-74 cells added at 1:1 ratio
Day 5 - Fresh GM added (no anti-CD-3 or IL-2 added)
Day 7 - Adjust to 5 × $10^5$ cells/ml with GM; anti-CD-3 and IL-2 added)
Day 10 - Cat inoculated with both control and mixture; 3.51 × $10^7$ cells total)

The cat was FeLV positive at the time of inoculation. By Jul. 19, 1994, all test for FeLV were negative. On Aug. 9, 1994, the cat was weakly positive by ELISA, but negative by IFA assay of peripheral blood smears. The cat was re-tested on Sep. 8, 1994 and both serum and salivary ELISA assays again were negative. PBL smears were not done. On Dec. 16, 1994, salivary ELISA was slightly positive, IFA positive, and serum antibody positive. As of Jul. 11, 1995, some 12 months post inoculation, Lady Jane was FeLV negative by all 3 assays, and remains well and clinically normal (active, asymptomatic, and healthy).

CAT 2

"Chubber Baby", a 2 year old male DSH cat, was diagnosed FeLV positive by ELISA tests of saliva and blood. Blood smears were also positive by IFA. On Aug. 3, 1994, popliteal lymph nodes were removed and prepared as described in Material and Methods. On day 2, the ln cells were co-incubated at a 1:1 ratio with L-74 cells. The medium was changed again on day 5, and on the 8th day 2.48×$10^8$ cells were inoculated by IV infusion (Aug. 10, 1994). The growth of the cells for inoculated are set forth below.

TABLE 2

| Day in Culture* | Living (× $10^7$) | Total (× $10^7$) | % Viable |
|---|---|---|---|
| 1 | 6.43 | 6.43 | 100 |
| 2 | 9.6 | 11.8 | 81 |
| 3 | 14.1 | 18.6 | 76 |
| 5 | 6.43 | 20.0 | 32 |
| 6 | 7.2 | 12.2 | 59 |
| 8 | 12.0 | 25.0 | 60 |
| Inoculated | 12.0 | 24.1 | 50 |

*Day 2 - FL-74 and IL-2 added (no anti-CD-3 added)
Day 5 - Adjusted concentration to 5 × $10^5$ cells/ml Prior to infusion, the cat appeared clinically normal, its BUN was normal (20), and its temperature was 102.6° F. About one hour following cell infusion, its temperature spiked to 106° F., while other parameters were normal. The cat remained IFA positive and gained 0.38 pounds from Aug. 10 to Sep. 8, 1994, then lost 0.75 lbs to Sep. 22, 1994. Concomitantly, the cat developed oral lesions and a decreased PCV. A viral URI was noted on Oct. 4, 1994. The cat was moderately depressed on Oct. 20, and by Nov. 2, 1994 its weight had dropped to 7.25 lbs and it had a PCV of 8.0 at which time the cat was euthanized.

CAT 3

"Half-Pint", a 2 year old DSH male cat was examined on Aug. 3, 1994. The cat FeLV (+) and a popliteal lymph node was removed and the cells were expanded in culture as described. Cells were infused on Aug. 10, 1994 at a concentration of $2.8 \times 10^8$ cells. The growth of the cells for inoculation is set forth in Table 2.

TABLE 3

| Day in Culture* | Living (× $10^7$) | Total (× $10^7$) | % Viable |
|---|---|---|---|
| 1 | 21.0 | 21.0 | 100 |
| 2 | 13.8 | 19.6 | 70 |
| 3 | 18.9 | 27.0 | 70 |
| 5 | 6.64 | 18.4 | 36 |
| 6 | 1.26 | 8.3 | 15 |
| 8 | 10.2 | 18.8 | 54 |
| Inoculated | 10.0 | 24.8 | 40 |

*Day 2 - FL-74 and IL-2 added (no anti-CD-3 added)
Day 5 - Adjusted concentration to $5 \times 10^5$ cells/ml The cat's weight decreased 0.23 lbs by Aug. 24 and by Sep. 15, 1994 it weighed 7.75 lbs, a loss of 0.5 lbs from Aug. 10. Its BUN was 70 and the PCV was 10. The animal was near death and was euthanized. A bone marrow smear was prepared and examined by a Board Certified veterinary pathologist who filed the following report:

Cellularity appears normal; M/E=10:1; orderly maturation of granulocytic series, megakaryocytes adequate; 19% small lymphocytes, slight increase in plasma cells; only a few erythroid precursors present with disproportionate number of immature forms; hemosiderin present, no etiologic agents or neoplastic cells detected.

Interpretation: Erythroid hypoplasia and lymphoid hyperplasia. These changes are not specific. Possible causes include FeLV infection, lack of stimulation by erythropoietin due to chronic renal disease, or anemia of chronic disease.

This report is consistent with a diagnosis of chronic renal disease and not necessarily a result of FeLV infection.

CAT 4

"Star", a 6 year old female Himalayan cat, was ill and determined to be FeLV positive on Aug. 3, 1994. Clinically, the cat was moribund, anorexic, and losing weight. Its temperature was 104.2° F., PCV of 36, pulse of 215, respiration of 20, BUN of 20, S.P. of 72, and weighed 4.75 lbs.

Popliteal lymph nodes were removed and the cells expanded as shown in Table 4.

TABLE 4

| Day in Culture* | Living (× $10^7$) | Total (× $10^7$) | % Viable |
|---|---|---|---|
| 1 | 24.0 | 24.0 | 100 |
| 2 | 17.7 | 21.5 | 82 |
| 3 | 13.9 | 18.3 | 75 |
| 5 | 13.4 | 23.3 | 58 |
| 6 | 96.8 | 161 | 59 |
| 8 | 19.0 | 29.0 | 65 |

TABLE 4-continued

| Day in Culture* | Living (× $10^7$) | Total (× $10^7$) | % Viable |
|---|---|---|---|
| Inoculated | 18.4 | 28.0 | 66 |

*Day 2 - FL-74 and IL-2 added (no anti-CD-3 added)
Day 5 - Adjusted concentration to $5 \times 10^5$ cells/ml On Aug. 10, 1994, the cat was determined to be Stage III and there was little change in the condition of the cat from the August 3rd examination. Its temperature was 104° F. and it weighed 4.75 lbs. It displayed upper right maxillary swelling due to an abscessed tooth and was given 0.3 ml of lincomycin. Star's temperature spiked to 105° F. about one hour post infusion of the cells.

On Aug. 24, 1994, Star was clinically normal with a temperature of 101.6° F. Star's body weight had increased to 4.87 lbs. By September 8, the cat's weight had increased to 5.25 lbs, its temperature was normal with blood smear and saliva FeLV positive. On October 4, the cat had URI with a slight temperature and weighed 6.25 lbs, while on October 20 its weight had increased to 7.0 lbs and was in good health.

More remarkable is the variation in its viral status. Both salivary ELISA assays and PBL smears were positive on Oct. 4, 1994, while the IFA became negative on October 20 and remained negative at the time of last testing on Dec. 16, 1994. The saliva test showed a weak (+) from October 20 until December 16 with a negative test on November 30 and November 30th. On Dec. 16, 1994, saliva was slightly FeLV (+) and IFA negative.

On Jan. 20, 1995, the cat weighed 7.5 lbs and was in good health. Again, on Aug. 10, 1995 (one year after treatment), the cat was FeLV negative by IFA. The cat remains clinically normal and in good health.

CAT 7

"Taffy", a 1½ year old female DSH cat, was classified Stage III on Oct. 7, 1994. A popliteal node was removed and processed as described in the Materials and Methods section, supra, with the exception that at 24 hours after culture initiation, FL 74 cells were added to the culture at a ratio of 1 FL 74 cell to 100 lymphocyte cells. On October 14, the cat was infused with $3.9 \times 10^8$ cultured lymphocyte cells. The cat was moderately anorexic and weighed 7.5 pounds.

TABLE 5

| Day in* Culture | Total (× $10^7$) | % Viable |
|---|---|---|
| 0 | 3.38 | 100 |
| 1 | 3.59 | 90 |
| 2 | 7.3 | 88 |
| 3 | 15.3 | 91 |
| 4 | 17.16 | 86 |
| 5 | 20.02 | 89 |
| 6 | 28.9 | 90 |
| 7 | 39.5 | 90 |

*Day 2 - 1 FL74:100 LN cells
Day 5 - Added ½ cell volume
Day 7 - Cat infused. Saved aliquot viable for 93 days The cat was re-examined on October 25 and had lost 0.5 lbs, but had started eating normally and was FeLV (+). When examined on November 17, she weighed 8 lbs and remained FeLV (+). When examined on November 17, she weighed 8 pounds and remained FeLV (+). On Dec. 16, 1994, the cat remained virus positive, but appeared normal and weighed 8.25 lbs. On Dec. 30, 1994, she had a mild URI, but was otherwise healthy. The PCV was normal and the cat weighed 8.75 lbs. On Jan. 19, 1995, the cat remained in good health while still FeLV (+).

CAT 10

A no-name, black-and-white, long-hair, intact, 4 week pregnant female cat tested FeLV positive by IFA, but not by saliva/blood ELISA. It had a weight of 5.35 lbs, pulse of 180, respiration rate of 20, and its BUN and TSP were acceptable. A popliteal ln was excised and expanded in accordance with the described protocol, but without FL74 cells. The cells were infused on Apr. 11, 1995. Clinical examination on Aug. 30, 1995 revealed a temperature of 102° F., pulse of 190, respiration rate of 15, weight of 3.3 lbs; urinalysis, pH of 6.0, SG of 1.030, and no blood. This cat also tested FeLV negative by ELISA assay, but was not tested by IFA.

CAT 12

"Precious", an orange, 8 month old, spayed female cat tested FeLV positive by IFA and saliva on Mar. 29, 1995. It had a temperature of 101.6° F., pulse of 180, respiration rate of 20, weight of 4.25 lbs, BUN of 20, PCV of 26, and Classified Stage II. Expanded cells were infused on April 11. On June 10, the cat was FeLV negative by ELISA, weighed 6 pounds, and appeared healthy. A clinical examination on August 30 revealed a temperature of 102° F., pulse rate of 180, respiration rate of 20, weight of 6.2 lbs; and urinalysis, pH of 6.0, SG of 1.030, with no blood present. This cat was FeLV negative by ELISA and IFA assays when tested on Sep. 1, 1995.

CAT 13

"Henry" was a neutered, long hair, 2 year old male cat with a weight of 9.75 lbs, BUN of 20, PCV of 35, slightly bloody urine, temperature of 100, pulse rate of 180, and had slightly enlarged lymph nodes. This cat was a Stage II FeLV cat. The ln cells were mixed with FL74 cells at a ratio of 1:100 and the expanded cells were infused on Apr. 11, 1995. The cat tested FeLV positive on May 5 and July 14; however, it remains clinically normal and healthy. On Aug. 27, 1995, a clinical examination revealed a temperature of 101.8° F., pulse rate of 190, respiration rate of 35, weight of 9.5 lbs; urinalysis of pH of 6.0, SG of 1.020; PCV of 29.4; and FeLV positive by ELISA and IFA.

CAT 14

"Hal" was a black, DSH, neutered male, FeLV cat that had a temperature of 102° F., pulse rate of 180, respiration rate of 20, BUN of 20, normal urine, weight of 7.25 lbs, and PCV of 37. No FL74 cells were used in the culture. Cells were infused on Apr. 18, 1995. On May 2, the cat was FeLV positive by saliva, had a temperature of 101.6° F., and weighed 7.75 lbs. The cat had a slight case of diarrhea, flaky skin, but was eating well. The cat appeared normal. On May 27, the cat was FeLV positive by saliva assay, had a temperature of 102.2° F., weighed 8.12 lbs and appeared clinically normal. On July 11 the cat again was FeLV positive by saliva and weighed 8.87 lbs.

On Aug. 12, 1995, the cat still was FeLV (+) by IFA assay. Clinically, however, the cat has improved with a weight gain to 13 pounds (up from 7.25 lbs when treated). On Aug. 10, 1995, a ln was removed for cytotoxic studies which will be reported below.

A portion of the expanded cells had been frozen (liquid nitrogen) and saved. These frozen cells were thawed, washed with phosphate buffered saline, and processed as described for infusion. On Sep. 18, 1995, $5 \times 10^7$ of these thawed cells were infused into the cat.

CAT 17

"Tripper" was a neutered male, LH, grey tiger cat that was FeLV positive Stage I on May 4, 1995. The cat weighed 12.25 lbs, had a BUN ca. 50, temperature of 102° F., pulse of 180, respiration rate of 20, PCV of 26, and serum protein count of 6.8. On May 11, 1995, $2.8 \times 10^7$ cells were infused. There were too few cells to harvest on day 0 for PCR analysis. On June 2, the cat still tested FeLV+, had a temperature of 101.4° F. and weighed 12 lbs. The cat did well for approximately 6 weeks, then began to lose weight with anemia. The cat was euthanized on Jul. 24, 1995.

CAT 18

Originally, the veterinarian treating "Bambi" had difficulty in locating and removing a popliteal ln. The yield of cells was small with little growth by mitogenic stimulation. On May 11, 1995, a mesenteric ln was removed and prepared according to the described protocol. The cat's clinical signs were: temperature of 102° F., pulse of 180, respiration rate of 20, weight of 15.0 lbs, PCV of 29, serum proteins of 6.0, and BUN of 20. One million cells were frozen on day 0 and day 7 of expansion for PCR analysis. On both day 0 and day 7, the cells analyzed by PCR to be negative for the FeLV gene sequences.

On June 2, the cat appeared clinically normal, except for some slight diarrhea. The cat was reported to be eating normally. The cat weighed 12.5 lbs and was weakly FeLV positive by saliva. On June 19, the cat's clinical signs were normal, temperature of 103° F. and weight of 12.75 lbs. The cat was FeLV (−) by plasma, but FeLV (+) by peripheral blood smears. On July 11, August 10, and Sep. 1, 1995, the cat again was FeLV (−) by plasma IFA and by salivary ELISA on Sep. 1, 1995.

CAT 19

"Andy" was a Stage III cat with a temperature of 101.6° F., pulse of 180, respiration rate of 20, serum proteins of 6.2, BUN of 80, PCV of 20, and weight of 8.75 lbs. The cat was FeLV+by saliva, PBL, and serum. One million cells were frozen on day 1 and day 8 for PCR analysis. Both samples were positive by PCR for FeLV gene sequences. Cell infusion therapy was initiated on Jun. 2, 1995.

On August 16, the BUN was 80 and the PCV had doubled to 38, indicating good bone marrow function and no anemia. The cat was downgraded to Stage I by its veterinarian. In addition, at the time of treatment, the cat had severe gingivitis and teeth problems, which by August 16 had been resolved into normal gingiva. Furthermore, the cat has gained 1.25 lbs and is doing well clinically. On Aug. 17, 1995, a ln was removed for cytotoxic assays which will be reported below. The cat still was FeLV (+) by saliva IFA and antibody positive.

CAT 20

A no-name, intact 8 month-old, yellow, short-hair male cat had a temperature of 100.6° F., a pulse of 180, respiration rate of 20, weight of 6.37 lbs, and was FeLV+by saliva, PBL smears, and serum. The cat also had a PCV of 35, BUN of 20, and serum proteins of 7.0. A popliteal ln was removed and processed according to the described protocol. One million cells were frozen on day 0 and day 7 for PCR analysis. Cell infusion therapy was initiated on Jun. 22, 1995.

On Aug. 28, 1995, the cat was examined with the following results being recorded: temperature of 102° F., pulse rate of 160, respiration rate of 18, weight of 6.4 lbs, and urinalysis of pH of 6.0, SG of 1.020, and heamturia negative. The cat also was FeLV positive by ELISA and by peripheral blood smear.

A summary of the results reported for the cats described above is set forth in Table 6 below.

TABLE 6

| CAT NO. | STAGE | VIABLE CELLS INJECTED | GAIN (months) | VIRUS RESPONSE AND DURATION |
|---|---|---|---|---|
| 1 | I | $3.5 \times 10^7$ | 12 | FeLV (−) at 1 year post infusion |
| 2 | II | $1.2 \times 10^8$ | 3 | Died 3 mos. post infusion |
| 3 | II | $7.4 \times 10^7$ | 1 | Died 1.5 mos. post infusion |
| 4 | III | $1.4 \times 10^8$ | 10 | FeLV (−) at 12 months post infusion |
| 7 | III | $3.9 \times 10^8$ | 8 | FeLV (+), healthy |
| 10 | I | $1.3 \times 10^7$ | 2.5 | Good health at 3 months post infusion |
| 12 | I | $1.6 \times 10^7$ | 1.5 | FeLV (−) at 8 weeks post infusion |
| 13 | II | $6.4 \times 10^7$ | 1.5 | FeLV (−) at 6 weeks post infusion |
| 14 | II | $8.0 \times 10^7$ | 1.5 | FeLV (+) at 2 months post infusion |
| 17 | I | $3.6 \times 10^7$ | — | Euthanized 73 days post infusion |
| 18 | II | $1.8 \times 10^8$ | 1.0 | FeLV (−) at 1 month post infusion |
| 19 | III | $2.5 \times 10^8$ | 2.0 | FeLV (+) at 12 weeks |
| 20 | II | $6.0 \times 10^7$ | No gain | FeLV (+) at 10 weeks |

*number of months that the cat gained and maintained weight following therapy.

As noted in Table 6 above, Cats 1, 4, 12, and 18 all reverted from FeLV (+) to FeLV (−) after therapy. Further, even though cats 2 and 3 died shortly after therapy, clinically it was observed that their quality of life was improved between the time of infusion (therapy) and death.

As stated above and not clearly evident from Table 6 is the return to normal daily activities of many of the cats treated in accordance with the precepts of the present invention. This aspect of the present invention has been termed "Quality of Life" or "QOL" and is defined as the return to normal daily activities of the diseased cat, such as, play, normal estrous cycles, weight gain, good grooming habits, and normal physiological functions. Thus, even though a cat may be FeLV virus positive following treatment in accordance with the present invention, the ability of the instant therapy to return the cats to life of "normal" (normal for that particular cat) daily activities bestows a Quality of Life improvement to the cat and is a definite benefit of the instant invention. Table 7 explores the QOL of the cats described above.

TABLE 7

| CATS TREATED | REVERSION TO VIRUS NEGATIVE | IMPROVED QOL | DIED OR NO IMPROVEMENT |
|---|---|---|---|
| 13 | 5/13 | 10/13 | 3/13 |
| % Response | 38.5% | 76.9% | 23.1% |

It should be noted that PCR analysis was done with cells from cats 14–20 in order to determine if the cells from the lymph nodes contained FeLV gene sequences and whether the presence or absence of gene sequences affected the outcome of the therapy. Displayed in Table 8 are the results of these experiments.

TABLE 8

| Sample No. | Cat No. | Day | FeLV Genome Present |
|---|---|---|---|
| 1 | 14 | 0 | Yes |
| 2 | 15 | 0 | No |
| 3 | 16 | 0 | Yes |
| 4 | 16 | 7 | No |
| 5 | 17 | 7 | Yes |
| 6 | 18 | 0 | No |
| 7 | 18 | 7 | No |
| 8 | 19 | 1 | Yes |
| 9 | 19 | 8 | Yes |
| 10 | 20 | 0 | Yes |
| 11 | 20 | 7 | Yes |

With Day 0 samples, Cats 14, 16, 19, and 20 were positive, while cells from Cat 15 [FeLV (−)] and 18 were negative. Gene sequences were detected in day 7 samples from Cats 17, 19, and 20, while Cat 16 was negative. It should be noted that Cat 18 ln cells were negative for FeLV sequences at the initiation of culture and with the day 7 sample. Cat 18 also converted from FeLV (+) to FeLV (−) status in 6 weeks after cellular therapy.

EXAMPLE 2

As noted above, lymph nodes removed from cats 14 and 19 were subjected to phenotyping and cytotoxicity studies. Lymph nodes from each cat were subjected to expansion under three different conditions: IL-2 alone; IL-2 plus human anti-CD3 monoclonal antibody (Ortho Biotech, Raritan, N.J.); and IL-2 plus cat anti-CD3 monoclonal antibody (VMRD Inc., Spokane, Wash.). These results revealed that both the human and cat anti-CD3 monoclonal antibodies were not mitogenic—they do not modulate cell expansion. Apparently, only the IL-2 was mitogenic for cell expansion as reported herein.

Marker analysis of the lymph nodes of the cats revealed the expanded cells to be: 72–88% $CD3^+$ (T-cell), 23–38% $CD4^+$ (T-helper/inducer), and 34–48% $CD8^+$ (T-cytolytic/suppressor). Finally, cytotoxicity to FL74 cells in in vitro tests revealed that the expanded cells lyre FL74 cells in vitro (25–45% lysis at effector to target ratio of 40:1). It should be noted that return appears to optimize cell expansion and cytolytic activity.

SUMMARY

Thirteen cats received cell infusion therapy. The infusion was well tolerated. Cats usually became febrile about 1 hour post-infusion—fever resolved without specific therapy within 1 hour. The clinical and virologic responses to date as summarized in Table 6 reveal that 10 of the 13 symptomatic cats (Stages II to IV) have demonstrated clinical improvement. Virologic improvement, manifesting either as reduction or disappearance of serum and/or salivary FeLV antigen expression, was observed in 4 cats. Mitogenic expansion of the lns requires only the presence of IL2 as anti-CD3 monoclonal antibody (human and cat) is not mitogenic for expansion. Finally, the expanded lns lyse FL74 cells.

Further, it appears that certain conditions/disease processes may result in cat death independent of the inventive cell infusion therapy, e.g., anemia, which was believed to be responsible for feline mortality of some of the cats reported above. Thus, unless anemia can be treated independent of the FeLV disease, the instant cell infusion therapy may be superfluous in respect of preventing cat death. This may mean that certain screening of candidate cats for the instant treatment may be necessary, desirable, or convenient.

It appears that effector lymphocytes are the class of cells responsible for the FeLV mitigation seen in the test cats. Presently, it is unknown whether these effector lymphocytes are helper or cytotoxic T cells.

We claim:

1. A method for mitigating disease associated with Feline Leukemia Virus (FeLV) in a feline infected with FeLV, which comprises administering to said feline an effective amount of a therapeutic agent comprising lymph node lymphocytes (LNL) expressed from excised lymph nodes taken from an FeLV-infected feline in which said LNL have been subject to mitogenic stimulation by their culturing in the presence of Interleukin-2 for their expansion.

2. The method of claim 1, wherein the amount of Interleukin-2 ranges from between about 10 and 500 u/ml.

3. The method of claim 1, wherein said culturing further includes FeLV infected cells.

4. The method of claim 3, wherein said FeLV infected cells were inactivated prior to their culturing with said lymph node lymphocytes.

5. The method of claim 4, wherein said FeLV infected cells were heated for inactivation.

6. The method of claim 1, wherein said therapeutic agent is administered more than one time with a suitable time period elapsing between said administering.

7. The method of claim 2, wherein said therapeutic agent is administered more than one time with a suitable time period elapsing between said administering.

8. The method of claim 3, wherein said therapeutic agent is administered more than one time with a suitable time period elapsing between said administering.

9. The method of claim 4, wherein said therapeutic agent is administered more than one time with a suitable time period elapsing between said administering.

10. The method of claim 5, wherein said therapeutic agent is administered more than one time with a suitable time period elapsing between said administering.

* * * * *